United States Patent [19]
Baak et al.

[11] Patent Number: 5,908,939
[45] Date of Patent: Jun. 1, 1999

[54] METHOD OF MAKING D,L-A-TOCOPHEROL

[75] Inventors: Marcel Baak, Sissach, Switzerland; Werner Bonrath, Freiburg, Germany; Horst Pauling, Bottmingen, Switzerland

[73] Assignee: Roche Vitamins Inc., Parsippany, N.J.

[21] Appl. No.: 08/951,273

[22] Filed: Oct. 16, 1997

[30] Foreign Application Priority Data

Nov. 11, 1996 [EP] European Pat. Off. .............. 96118037

[51] Int. Cl.$^6$ .................................................. C07D 311/02
[52] U.S. Cl. ............................................................ 549/407
[58] Field of Search ............................................ 549/407

[56] References Cited

U.S. PATENT DOCUMENTS

| | | |
|---|---|---|
| 2,723,278 | 11/1955 | Surmatis et al. . |
| 3,444,123 | 5/1969 | Singer et al. . |
| 3,459,773 | 8/1969 | Moroe et al. . |
| 3,789,086 | 1/1974 | Frick et al. . |
| 4,634,781 | 1/1987 | Finnan . |
| 5,523,420 | 6/1996 | Lowack et al. . |
| 5,526,821 | 6/1996 | Armand . |
| 5,684,023 | 11/1997 | Riedl et al. . |
| 5,723,664 | 3/1998 | Sakaguchi et al. . |

FOREIGN PATENT DOCUMENTS

| | | |
|---|---|---|
| 12824 | 7/1980 | European Pat. Off. . |
| 658 552 | 6/1995 | European Pat. Off. . |
| 677522 | 10/1995 | European Pat. Off. . |

OTHER PUBLICATIONS

Chemical Abstract 103:104799d (1985).
Chemical Abstract 103:123731s (1985).
Chemical Abstract 110:32917r (1989).
Bergel, et al., "Vitamin E Synethesis of α–Tocopherol", Nature, 142:36 (1938).
Smith et al., "The Chemistry of Vatamin E: I. The Structure and Syntehsis of α–Tocopherol", Science, 88:37–38 (1938).
Smith et al., The Chemistry of Vitamin E: Condensation of Phenols and Hydroquinones with Allylic Alcohols . . . , J.Am. Chem. Soc. 61:2615–2618 (1939).
Y. Tachibana, "Preparation of Vitamin E Using Cation Exchange Resin Complexes of Metal Ions", Bull. Chem. Soc. Japan 50:2477–2478 (1977).
Mikami et al., "Metal Bis(trifluoromethylsulfonyl)amides as Highly Efficient Lewis Acid Catalysts for Acylation Reaction", Synlett 171–172 (1996).
Ishiohara et al., "A New Scandium Complex as an Extremely Active Acylation Catalyst", Synlett 265–266 (1996).
Kobayashi et al., "Metal Bis((perfluoroalkyl)sulfonyl)amides as Novel Lewis acid Catalysts in Diels–Alder Reaction", Chem Lett. 307–308 (1995).
Ishihara et al., "Practical Syntehsis of (±)–α–Tocopherol.", Synlett No. 11, pp. 1045–1046 (Nov., 1996).
Matsui et al., Synthesis of α–Tocopherol., Bull Chem. Soc. Japan, 68–3569–3571 (1995).
Abstract of Japanese Patent Application 07246338, 1995.
U.S. application No. 08/778,479, Bonrath., filed Jan. 3, 1997.
Matsui et al., Bull. Chem. Soc. Jpn., 68(12), 3569–3571, 1995.

*Primary Examiner*—Johann Richter
*Assistant Examiner*—Taofiq A. Solola
*Attorney, Agent, or Firm*—George W. Johnston; Dennis P. Tramaloni

[57] ABSTRACT

A process for the manufacture of d,1-α-tocopherol by the catalyzed condensation of trimethylhydroquinone with isophytol comprises carrying out the condensation in the presence of bis-(trifluoromethylsulphonyl)amine [$HN(SO_2CF_3)_2$] or a metal salt thereof of the formula Met [$N(SO_2CF_3)_2$]$_n$ (I), wherein Met signifies a metal atom selected from the group of lithium, boron, magnesium, aluminium, silicon, scandium, titanium, vanadium, manganese, iron, cobalt, nickel, copper, zinc, yttrium, zirconium, rhodium, palladium, silver, tin, lanthanum, cerium, neodymium, praseodymium, europium, dysprosium, ytterbium, hafnium, platinum and gold and n signifies the corresponding valency (1, 2, 3, or 4) of the metal atom Met, as the catalyst or of a combination of a metal salt of formula I and a strong Bronsted acid as the catalyst system in an organic solvent. The product of the process is the most active member of the vitamin E group.

25 Claims, No Drawings

METHOD OF MAKING D,L-A-TOCOPHEROL

BACKGROUND OF THE INVENTION

The present invention is concerned with a novel process for the manufacture of d,1-α-tocopherol by the catalyzed condensation of trimethylhydroquinone with isophytol. As is known, d,1-α-tocopherol is a diastereomer mixture of 2,5,7,8-tetramethyl-2-(4',8',12'-trimethyl-tridecyl)-6-chromanol (α-tocopherol), which is the most active and industrially most important member of the vitamin E group.

Various processes for the manufacture of d,1-α-tocopherol by the condensation of trimethylhydroquinone (TMHQ) with isophytol (IP) in the presence of a catalyst or catalyst system have already been described. These processes go back to the work of Karrer et al., Bergel et al. as well as Smith et al. [see Helv. Chim. Acta 21, 520 et seq. (1938), Nature 142, 36 et seq. (1938) and, respectively, Science 88, 37 et seq. (1938) and J. Am. Chem. Soc. 61, 2615 et seq. (1939)]. While Karrer et al. carried out the synthesis of d,1-α-tocopherol from TMHQ and phytyl bromide in the presence of anhydrous zinc chloride (a Lewis acid), not only Bergel et al. but also Smith et al. used TMHQ and phytol as starting materials. In the following years mainly modifications, e.g. alternative solvents and Lewis acids, were developed. From the work of Karrer et al. there was developed in the year 1941 a technically interesting process for the manufacture of d,1-α-tocopherol, which was based on the condensation of TMHQ with IP in the presence of the catalyst system zinc chloride/hydrochloric acid (U.S. Pat. No. 2,411,969). Later publications, e.g. Japanese Patent Publications (Kokai) 54380/1985, 64977/1985 and 226979/1987 [see Chemical Abstracts (C.A.) 103, 123731s (1985), C.A. 103, 104799d (1985) and, respectively, C.A. 110, 39217r (1989)], describe this condensation in the presence of zinc and zinc chloride ($ZnCl_2$) and a protonic acid, such as a hydrohalic acid, e.g. hydrochloric acid (HCl), trichloroacetic acid, acetic acid and the like, especially $ZnCl_2$/HCl, as the catalyst system.

The manufacture of d,1-α-tocopherol by the reaction of TMHQ with phytyl chloride or isophytol in the presence of boron trifluoride ($BF_3$) or its etherate ($BF_3Et_2O$) is described in German Offenlegungsschriften (DOS) 960720 and 1015446 as well as in U.S. Pat. Nos. 3,444,123 and 4,634,781. However, boron trifluoride has corrosive properties.

Also, the condensation of TMHQ with IP or phytol, which has been treated with ammonia or amines, in the presence of $ZnCl_2$/HCl or a Lewis acid, e.g. $BF_3$ or aluminium trichloride ($AlCl_3$), and hydrochloric acid as the catalyst system has been described in the patent literature, e.g. in DOS 2 606 830, U.S. Pat. No. 4,634,781 and European Patent Publication (EP) 100471. Again corrosion problems occur.

A further interesting method for the manufacture of d,1-α-tocopherol from TMHQ and IP comprises using isolated TMHQ-$AlCl_3$ complexes (DOS 1909164). This process variant avoids to a large extent the formation of undesired byproducts because it involves mild reaction conditions. The yield of d,1-α-tocopherol is given as 77% based on IP. The use of solvent mixtures, such as e.g. methylene chloride/nitromethane, is disadvantageous.

Using the reaction described in the literature of TMHQ with IP in the presence of $ZnCl_2$ in combination with acids such as trichloroacetic acid, acetic acid or acidic salts, such as sodium hydrogen sulphate, d,1-α-tocopherol cannot be manufactured in the required purity (about 85%) (see, for example, DOS 1909164).

A further application of $ZnCl_2$ - with the addition of bromine—in the condensation of TMHQ with IP is disclosed in Czechoslovakian Patent 205952.

A further method for the condensation of TMHQ with IP to d,1-α-tocopherol is effected using a mixture of silicic acid and aluminium oxide pre-treated with protonic acids (see DOS 2404621). This method gives d,1-α-tocopherol in 90% yield; the required excess of IP (based on TMHQ) is, however, disadvantageous.

The manufacture of d,1-α-tocopherol by the condensation of TMHQ with IP using ion exchangers in combination with metal ions ($Zn^{2+}$, $Sn^{2+}$ and $Sn^{4+}$) disclosed in Bull Chem, Soc. Japan 50, 2477 et seq. (1977) gives the product in 70–87.5% yield.

All processes using $ZnCl_2$ in combination with Bronsted acids as catalyst systems feature as a disadvantage the occurrence of corrosion problems and a potential contamination of the waste water with zinc ions.

The use of ion exchangers (Amberlyst® 15) as the catalyst for the condensation of TMHQ with IP is described in U.S. Pat. No. 3,459,773. However, the d,1-α-tocopherol could not be obtained in the requisite purity.

The manufacture of d,1-α-tocopherol in liquid or supercritical carbon dioxide by the condensation of TMHQ with IP in the presence of ion exchangers takes place according to EP 603 695 in about 85% yield.

The condensation in the presence of a catalyst system which consists of iron(II) chloride, metallic iron and hydrogen chloride gas is described in DOS 2160103 and U.S. Pat. No. 3,789,086. The formation of less byproducts is advantageous compared with the aforementioned process using zinc chloride and hydrochloric acid. However, corrosion problems and chloride contamination are equally disadvantageous.

An interesting alternative for the condensation of TMHQ with IP to d,1-α-tocopherol comprises using trifluoroacetic acid (EP 12824). Of advantage in this process are the good recyclization of the acid and the avoidance of hydrochloric acid. Disadvantageous are the facts that trifluoroacetic acid is relatively expensive and suitable materials for a production process are difficult to obtain.

The use of heterogeneous silicate-based catalysts (clays; especially zeolites) for the condensation is described in C.A. 100, 22833 (1984) and gives d,1-α-tocopherol in a yield of about 92%.

The use of heteropolytungsten acids as catalysts for the condensation of TMHQ with IP has been described for the first time in React. Kinet. Catal. Lett. 47, 59 et seq. (1992). d, 1-α-Tocopherol could be obtained in 90% yield with this process using toluene as the solvent. The separation of the catalyst and more precise experimental details, such as e.g. the dosage of the isophytol, are, however, not described in this literature reference. The excess of IP based on TMHQ is a disadvantage.

A further process described in the literature for the synthesis of d,1-α-tocopherol is based on the use of lathanide triflates, such as e.g. scandium trifluoromethanesulphonate. With a 10% excess of IP this process gives yields of 96–98% [EP 658 552; Bull. Chem. Soc. Japan 68, 3569 et seq. (1995)].

The use of scandium chlorides and other chlorides (yttrium, lanthanum etc.) on a carrier, e.g. bentonite or montmorillonite, as the catalyst for the condensation of TMHQ with IP has as disadvantages the need for a large amount of catalyst and an excess (about 10%) of IP [EP 677 522; Bull. Chem. Soc. Japan 69, 137 et seq. (1996)].

According to EP 694 544 the condensation of TMHQ with IP in isopropyl acetate catalyzed by ZnCl$_2$/HCl gives d,1-α-tocopherol in yields of 98.6% with a purity of 98.6%. Disadvantageous in this process are, in addition to the contamination of the waste water by zinc ions, the large "catalyst amounts" (e.g. 23.3 g of ZnCl$_2$ for 67 g of product) and the isophytol excess.

From the forgoing explanations it will be evident that the previously known processes have considerable disadvantages. Thus, corrosion problems occur in the case of all processes, when boron trifluoride is used toxicity problems with the boron trifluoride adducts also occur and when iron or zinc is used there is a contamination of the waste water with iron or zinc ions which is today no longer acceptable. In the case of some processes the formation of undesired byproducts, e.g. phytyltoluene and chlorophytols, is an especially serious problem.

SUMMARY OF THE INVENTION

The object of the present invention is to provide a process for the manufacture of d,1-α-tocopherol by the condensation of trimethylhydroquinone with isophytol in the presence of a catalyst which does not have the disadvantages of previously known procedures. In this respect, it is necessary that the catalyst used does not have a corrosive action, is non-toxic, does not contaminate the environment and catalyzes the desired reaction as selectively as possible and in high yields. Furthermore, the catalyst should display its activity already in really only catalytic amounts, and should be readily separable and re-usable several times.

In the scope of the present invention this object is achieved by carrying out the condensation of trimethylhydroquinone with isophytol in the presence of a particular amine catalyst and in an organic solvent. The condensation is effected according to the following Reaction Scheme which is presented conventionally:

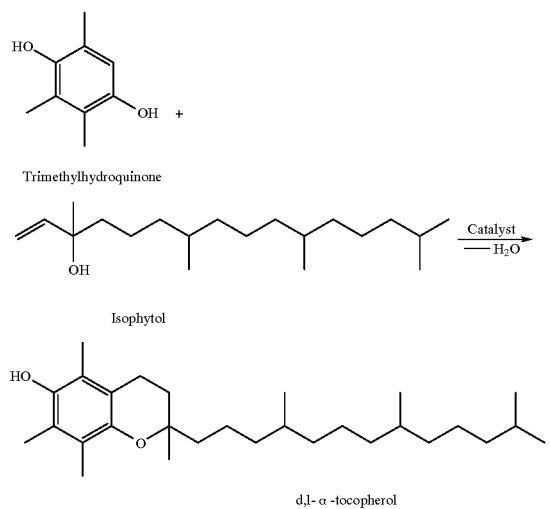

in which the catalyst is a particular amine catalyst the nature of which will be explained in more detail below. Moreover, the condensation is carried out in an organic solvent.

DETAILED DESCRIPTION OF THE INVENTION

The process in accordance with the invention for the manufacture of d,1-α-tocopherol by the catalyzed condensation of trimethylhydroquinone with isophytol comprises reacting trimethylhydroquinone and isophytol dispersed in an aprotic organic solvent in the presence of a catalytically effective amount of a catalyst which comprises bis-(trifluoromethylsulphonyl)amine [HN(SO$_2$CF$_3$)$_2$] or of a metal salt thereof of the formula:

  Met [N(SO$_2$CF$_3$)$_2$]$_n$   I wherein:

Met is a metal atom selected from the group of lithium, boron, magnesium, aluminium, silicon, scandium, titanium, vanadium, manganese, iron, cobalt, nickel, copper, zinc, yttrium, zirconium, rhodium, palladium, silver, tin, lanthanum, cerium, neodymium, praseodymium, europium, dysprosium, ytterbium, hafnium, platinum and gold; and n is the valency (1, 2, 3 or 4) of the metal atom, Met;

whereby the trimethylhydroquinone and isophytol are condensed to d,1-α-tocopherol. When a metal salt of formula I is used the catalyst may further comprise a strong Bronsted acid.

Not only bis-(trifluoromethylsuphonyl)amine, but also some of the metal salts of formula I are known compounds [see, for example, EP 364 340, Japanese Patent Publication (Kokai) 246 338/1995, DOS 19533711, Synlett 1996, 171–172, Synlett 1996, 265–266, Chem. Lett. 1995, 307–308 as well as the further literature references mentioned in this state of the art]. The metal salts of formula I which may still not be known can be produced according to methods known per se, namely from the corresponding metal acetates, oxides, hydroxides and alcoholates analogously to known methods. In the case of the aluminium salt and the zinc salt of bis-(trifluoromethylsulphonyl)amine (of the formula Al[N(SO$_2$CF$_3$)$_2$]$_3$ and, respectively, Zn[N(SO$_2$CF$_3$)$_2$]$_2$), these can also be produced from a corresponding alkylmetal or dialkylmetal hydride, e.g. diethylzinc or triethylaluminium or, respectively, diisobutylaluminium hydride.

The metal salts of the bis-(trifluoromethylsulphonyl)amine can be present in monomeric or polymeric form and, accordingly, formula I is intended to embrace all such forms. Further, these catalysts can be used in isolated form or produced in situ.

The Bronsted acid present in the catalyst is any conventional inorganic or organic acid of this type. Sulphuric acid, phosphoric acid and p-toluene-sulphonic acid are examples of Bronsted acids.

Solvents which can be used in the scope of the present invention are any conventional aprotic organic solvents. Preferred solvents are especially aliphatic and cyclic ketones, e.g., isobutyl methyl ketone and diethyl ketone and, respectively, cyclopentanone and isophorone; aliphatic and cyclic esters, e.g., ethyl acetate, isopropyl acetate and, respectively, γ-butyrolactone; and aromatic hydrocarbons, e.g., toluene and xylene. In the condensation reaction of the invention, it is preferred to remove the resulting water by azeotropic distillation.

The temperature at which the reaction of the invention is carried out is not critical, so long as the production of some d,1-α-tocopherol takes place. Preferably, the condensation is effected at temperatures between about 80° C. and about 150° C., more preferably between about 100° C. and about 140° C., especially between about 105° C. and about 120° C.

The ratio of reactants, trimethylhydroquinone and isophytol used in the process of the invention is not critical, so long as some d,1-α-tocopherol is produced. Preferably, about equimolar amounts of the two educts (reactants), trimethylhydroquinone and isophytol, are used. Also, the amount of catalyst used in the process of the invention is not critical, so long as some d,1-α-tocopherol is produced. The amount of catalyst is preferably about 0.08–0.3 mol % in the case of the bis-(trifluoromethylsulphonyl)amine and conveniently about 0.5–4 mol % in the case of a metal salt of formula I, in each case based on the amount of educt (trimethylhydroquinone or isophytol) which is present in lesser amount. Where the catalyst comprises the metal salt of formula I and a strong Bronsted acid, the amount of metal salt is preferably about 0.1–4 mol % and the amount of Bronsted acid is preferably about 0.01–0.5 mol %, in each case based on the amount of educt which is present in lesser amount.

The amount of aprotic organic solvent is not critical, so long as some d,1-α-tocopherol is produced. Preferably, about 25–100 ml, more preferably about 40–50 ml, of the aprotic organic solvent are used per 100 mmol of the one or the other educt, whichever one is present in lesser amount.

The process in accordance with the invention can be carried out operationally by any conventional means. For example, the reaction of the invention may be carried out by adding isophytol dropwise to a suspension of trimethylhydroquinone and catalyst in a solvent. The rate at which the isophytol is added is not critical. Conveniently, isophytol is added dropwise over a period 0.5 to 5 hours. After completion of the isophytol addition and an appropriate subsequent reaction period the working-up is effected by procedures conventionally used in organic chemistry.

The process in accordance with the invention enables the catalyst used to be separated readily and to be re-used several times.

Advantages in the use of the catalyst in the process in accordance with the invention are, in addition to high yields of d,1-α-tocopherol, the avoidance of corrosion, the avoidance of waste water contamination with heavy metal ions, the high selectivity as well as the enabled ready separation from unreacted trimethylhydroquinone.

Moreover, it is notable that neither the bis-(trifluoromethylsulphonyl)amine nor a derivative thereof has previously been used for condensation reactions, not to mention for the manufacture of d,1-α-tocopherol. Furthermore, no amines have hitherto been used as catalysts for the condensation of trimethylhydroquinone with isophytol to produce d,1-α-tocopherol.

The process in accordance with the invention is illustrated by the following Examples:

EXAMPLE 1

31.4 g (200 mmol) of trimethylhydroquinone (TMHQ; 97%) are suspended in 100 ml of toluene under reflux and under argon as the protective gas in a 500 ml four-necked round flask fitted with a gas inlet tube, stirrer, thermometer, water separator and dosage device. The suspension is treated with 0.7 ml of a solution of 1.37 g of bis-(trifluoromethylsulphonyl)amine in 10 ml of toluene (containing about 84 mg of catalyst). To this suspension are subsequently added at 140° C. (oil bath temperature) 73.02 ml (200 mmol) of isophytol (IP; 96%) at a rate of addition of 2.4 ml per minute (addition time=30 minutes). Subsequently, the mixture is boiled at 140° C. (oil bath temperature) for a further 30 minutes. During the reaction the TMHQ passes into solution, and the internal temperature of the reaction mixture rises from 110° C. to 120° C. After completion of the reaction a dark brown solution is obtained. After cooling to room temperature the reaction solution is transferred into a 1 l round flask and concentrated under reduced pressure at 50° C. and 20 mbar (2 kPa).

In this manner there are obtained 90% of theory of d,1-α-tocopherol.

EXAMPLES 2–36

According to the procedure described in Example 1, equimolar amounts of TMHQ and IP are condensed with each other in the presence of bis(trifluoromethylsulphone) imide or a metal salt thereof of formula I in order to produced, 1-α-tocopherol. The respective variable details of the operation as well as the results are compiled in the following Table in which, inter alia, the catalyst is represented in each case by its chemical formula:

TABLE

| Example No. | Catalyst | Catalyst Amount | mmol TMHQ/IP | Solvent | Solvent amount | d,l-α-Tocopherol Yield |
|---|---|---|---|---|---|---|
| 2 | $HN(SO_2CF_3)_2$ | 1.37 g | 200 | Isobutyl methyl ketone | 100 ml | 92.5% |
| 3 | " | " | " | Isopropyl acetate | " | 91.7% |
| 4 | " | " | " | Ethyl acetate | " | 87.2% |
| 5 | $Mg[(SO_2CF_3)_2]_2$ | 1.17 g | 100 | Toluene | 45 ml | 92.6% |
| 6 | " | 1.25 g | " | Isobutyl methyl ketone | " | 75% |
| 7 | $Al[N(SO_2CF_3)_2]_3$ | 1.73 g | " | Toluene | " | 78% |
| 8 | " | 0.56 g | " | " | " | 89% |
| 9 | $Sc[(SO_2CF_3)_2]_3$ | 0.27 g | " | " | " | 86.6% |
| 10 | $V[N(SO_2CF_3)_2]_3$ | 1.78 g | " | " | " | 76.3% |
| 11 | $Mn[N(SO_2CF_3)_2]_2$ | 1.23 g | " | " | " | 92.5% |
| 12 | " | " | " | Isobutyl methyl ketone | " | 87.9% |
| 13 | " | " | " | Isopropyl acetate | " | 77.1% |
| 14 | $Fe[(SO_2CF_3)_2]_2$ | 0.31–1.23 g | " | Toluene | " | 86.2–91.6% |
| 15 | $Fe[N(SO_2CF_3)_2]_3$ | 1.79 g | " | " | " | 85.5% |
| 16 | $Co[N(SO_2CF_3)_2]_2$ | 1.24 g | " | " | " | 87.2% |
| 17 | $Ni[N(SO_2CF_3)_2]_2$ | 1.25 g | " | " | " | 91.3% |
| 18 | $Cu[N(SO_2CF_3)_2]_2$ | 0.05 g | " | " | " | 86% |
| 19 | $Zn[N(SO_2CF_3)_2]_2$ | 0.07–1.25 g | " | " | " | 86–93% |
| 20 | " | 1.24 g | " | Isobutyl methyl | " | 90% |

TABLE-continued

| Example No. | Catalyst | Catalyst Amount | mmol TMHQ/IP | Solvent | Solvent amount | d,l-α-Tocopherol Yield |
|---|---|---|---|---|---|---|
| | | | | ketone | | |
| 21 | Y[N(SO$_2$CF$_3$)$_2$]$_3$ | 0.45 g | " | Toluene | " | 89.5% |
| 22 | Pd[N(SO$_2$CF$_3$)$_2$]$_2$ | 1.34 g | " | " | " | 80% |
| 23 | AgN(SO$_2$CF$_3$)$_2$ | 1.34 g | " | " | " | 82% |
| 24 | Sn[N(SO$_2$CF$_3$)$_2$]$_2$ | 1.36 g | " | " | " | 84.8% |
| 25 | La[N(SO$_2$CF$_3$)$_2$]$_3$ | 1.96 g | " | " | " | 91.1% |
| 26 | " | 2.00 g | " | Isobutyl methyl ketone | " | 92.6% |
| 27 | " | " | " | Isopropyl acetate | " | 90.3% |
| 28 | Ce[N(SO$_2$CF$_3$)$_2$]$_4$ | 1.96 g | " | Toluene | " | 90.2% |
| 29 | Nd[(SO$_2$CF$_3$)$_2$]$_3$ | 1.97 g | " | " | " | 89.5% |
| 30 | Pr[(SO$_2$CF$_3$)$_2$]$_3$ | 1.96 g | " | " | " | 92.8% |
| 31 | Eu[N(SO$_2$CF$_3$)$_2$]$_3$ | 1.99 g | " | " | " | 82.7% |
| 32 | Dy[(SO$_2$CF$_3$)$_2$]$_3$ | 2.00 g | " | " | " | 87.5% |
| 33 | Yb[N(SO$_2$CF$_3$)$_2$]$_3$ | 2.03 g | " | " | " | 88.6% |
| 34 | Hf[N(SO$_2$CF$_3$)$_2$]$_4$ | 2.60 g | " | " | " | 77.5% |
| 35 | B[N(SO$_2$CF$_3$)$_2$]$_3$ | 1.00 g | 200 | " | 100 ml | 88.4% |
| 36 | Rh$_2$[N(SO$_2$CF$_3$)$_2$]$_4$ | 1.2 g | " | " | " | 88.4% |

EXAMPLE 37

31.8 g (200 mmol) of TMHQ (98.5%) are suspended in 90 ml of toluene under reflux and under argon as the protective gas in a 500 ml four-necked round flask fitted with a gas inlet tube, stirrer, thermometer, water separator and dosage device. The suspension is treated with 1.15 g of bis-(trifluoromethylsulphonyl)amine lithium salt and 80 mg of p-toluenesulphonic acid. The further procedure is carried out as described in Example 1.

In this manner there are obtained 92% of theory of d,l-α-tocopherol.

We claim:

1. A process for making d,l-α-tocopherol by the catalyzed condensation of trimethylhydroquinone with isophytol, which process comprises reacting trimethylhydroquinone with isophytol dispersed in an aprotic organic solvent in the presence of a catalytically effective amount of a catalyst which comprises bis-(trifluoromethylsulphonyl)amine or a metal salt thereof of the formula:

$$\text{Met } [\text{N}(\text{SO}_2\text{CF}_3)_2]_n \qquad \text{I}$$

wherein:

Met is a metal atom selected from the group of lithium, boron, magnesium, aluminium, silicon, scandium, titanium, vanadium, manganese, iron, cobalt, nickel, copper, zinc, yttrium, zirconium, rhodium, palladium, silver, tin, lanthanum, cerium, neodymium, praseodymium, europium, dysprosium, ytterbium, hafnium, platinum and gold; and n is the valency of the metal atom, Met, whereby the trimethylhydroquinone and isophytol are condensed to produce d,1-α-tocopherol.

2. The process of claim 1 wherein the catalyst comprises bis-(trifluoromethylsulphonyl)amine and the reaction is carried out at a temperature in the range from about 80° C. to about 150° C.

3. The process of claim 2 wherein the amount of bis-(trifluoromethylsulphonyl)amine is in the range from about 0.08 to about 0.3 mol % of the reactant which is present in lesser amount.

4. The process of claim 1 wherein the aprotic organic solvent is an aliphatic or cyclic ketone, an aliphatic or cyclic ester, or an aromatic hydrocarbon.

5. The process of claim 4 wherein the aprotic organic solvent is isobutyl methyl ketone, ethyl acetate, isopropyl acetate or toluene.

6. The process of claim 5 wherein the amount of organic solvent is in the range from about 25 ml to about 100 ml per 100 mmol of whichever reactant is in lesser amount.

7. The process of claim 6 wherein the amount of organic solvent is in the range from about 40 ml to about 50 ml per 100 mmol of whichever reactant is in lesser amount.

8. The process of claim 7 wherein the reaction is carried out at a temperature in the range from about 100° C. to about 140° C.

9. The process of claim 8 wherein the reaction is carried out at a temperature in the range from about 105° C. to about 120° C.

10. The process of claim 1 wherein the catalyst comprises a compound of formula I.

11. The process of claim 10 wherein the amount of the compound of formula I is in the range from about 0.5 to about 4 mol % of the reactant which is present in lesser amount, and the reaction is carried out at a temperature in the range from about 80° C. to about 150° C.

12. The process of claim 11 wherein the aprotic organic solvent is an aliphatic or cyclic ketone, an aliphatic or cyclic ester, or an aromatic hydrocarbon.

13. The process of claim 12 wherein the aprotic organic solvent is isobutyl methyl ketone, ethyl acetate, isopropyl acetate or toluene.

14. The process of claim 13 wherein the amount of organic solvent is in the range from about 25 ml to about 100 ml per 100 mmol of whichever reactant is in lesser amount.

15. The process of claim 14 wherein the amount of organic solvent is in the range from about 40 ml to about 50 ml per 100 mmol of whichever reactant is in lesser amount.

16. The process of claim 15 wherein the reaction is carried out at a temperature in the range from about 100° C. to about 140° C.

17. The process of claim 16 wherein the reaction is carried out at a temperature in the range from about 105° C. to about 120° C.

18. The process of claim 10 wherein the catalyst further comprises a strong Bronsted acid.

19. The process of claim 18 wherein the amount of the compound of formula I is in the range from about 0.1 to about 4 mol % of the reactant which is present in lesser amount, the amount of Bronsted acid is about 0.01–0.5 mol % of the reactant which is present in lesser amount, and the reaction is carried out at a temperature in the range from about 80° C. to about 150° C.

20. The process of claim 19 wherein the aprotic organic solvent is an aliphatic or cyclic ketone, an aliphatic or cyclic ester, or an aromatic hydrocarbon.

21. The process of claim 20 wherein the aprotic organic solvent is isobutyl methyl ketone, ethyl acetate, isopropyl acetate or toluene.

22. The process of claim 21 wherein the amount of organic solvent is in the range from about 25 ml to about 100 ml per 100 mmol of whichever reactant is in lesser amount.

23. The process of claim 22 wherein the amount of organic solvent is in the range from about 40 ml to about 50 ml per 100 mmol of whichever reactant is in lesser amount.

24. The process of claim 23 wherein the reaction is carried out at a temperature in the range from about 100° C. to about 140° C.

25. The process of claim 24 wherein the reaction is carried out at a temperature in the range from about 105° C. to about 120° C.

* * * * *